United States Patent
Simas, Jr. et al.

(10) Patent No.: US 8,016,796 B2
(45) Date of Patent: Sep. 13, 2011

(54) SAFETY NEEDLE DEVICE WITH SNAP FEATURE AND METHOD OF MAKING SAME

(75) Inventors: Robert Simas, Jr., Norfolk, MA (US); David MacLean, Swanzey, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 1867 days.

(21) Appl. No.: 11/138,553

(22) Filed: May 27, 2005

(65) Prior Publication Data

US 2006/0270979 A1 Nov. 30, 2006

(51) Int. Cl.
*A61M 5/32* (2006.01)
*A61M 5/00* (2006.01)

(52) U.S. Cl. ........................ 604/192; 604/110
(58) Field of Classification Search .................. 604/110, 604/263, 192, 198, 197
See application file for complete search history.

(56) References Cited

U.S. PATENT DOCUMENTS

| | | | |
|---|---|---|---|
| 4,982,842 A | | 1/1991 | Hollister |
| 5,085,640 A | * | 2/1992 | Gibbs ............................ 604/110 |
| 5,139,489 A | | 8/1992 | Hollister |
| 5,154,285 A | | 10/1992 | Hollister |
| 5,232,454 A | | 8/1993 | Hollister |
| 5,232,455 A | | 8/1993 | Hollister |
| 5,277,311 A | | 1/1994 | Hollister |
| 5,423,765 A | | 6/1995 | Hollister |
| 5,662,617 A | * | 9/1997 | Odell et al. .................... 604/192 |

(Continued)

FOREIGN PATENT DOCUMENTS

| | | |
|---|---|---|
| JP | 8-107933 | 4/1996 |
| JP | 2003-220139 | 8/2003 |
| JP | 2003-275308 | 9/2003 |

OTHER PUBLICATIONS

"Boss." Merriam-Webster Online Dictionary. 2009. Merriam-Webster Online. Jan. 5, 2009 <http://www.merriam-webster.com/dictionary/boss>.*

*Primary Examiner* — Nicholas D Lucchesi
*Assistant Examiner* — Nathan R Price
(74) *Attorney, Agent, or Firm* — Louis Woo

(57) ABSTRACT

The present invention safety device is a one-piece needle assembly that has a base and a housing pivotally connected to the base. The base has a distal portion to which a needle is fitted. At the base there is formed longitudinally along its distal portion a catch mechanism that may be in the form of an anchor projection. At the back wall of the housing there is extended another catch mechanism that may be configured in the form of two clasping fingers. Also providing in the housing is an integral hook. As the housing and the base are pivoted relative to each other, and as the needle makes contact with the hook, the respective catch mechanisms at the base and the housing also make contact with each other, resulting in the coupling of the catch mechanisms and the coupling of the needle to the hook. As a result, the catch mechanisms are interlocked and the needle is fixedly retained by the hook within the housing. The catch mechanisms may also be configured as a hook and a latch in the form of a rib with an opening whereto the hook is fixedly coupled. The catch mechanisms may further be configured as respective interlockable pairs of loops and bosses. The gauge of the needle may be determined by the color of both the base and the housing, which are molded as a unitary single unit.

19 Claims, 6 Drawing Sheets

U.S. PATENT DOCUMENTS

| | | |
|---|---|---|
| RE37,110 E | 3/2001 | Hollister |
| RE37,252 E | 7/2001 | Hollister |
| 6,328,713 B1 * | 12/2001 | Hollister ............... 604/192 |
| 2004/0078007 A1 * | 4/2004 | Nguyen ............... 604/263 |
| 2005/0049560 A1 | 3/2005 | Hauri |
| 2005/0054986 A1 | 3/2005 | Simpson et al. |

* cited by examiner

SAFETY NEEDLE DEVICE WITH SNAP FEATURE AND METHOD OF MAKING SAME

RELATED APPLICATION

The present application is related to application Ser. No. 11/029,371 filed on Jan. 6, 2005.

FIELD OF THE INVENTION

The present invention relates to needle protection devices and more particularly to a needle assembly, adaptable to be used with a syringe, that includes mechanisms at its base and housing that coact to non-removably retain the housing and the base in a secured relationship, at the same time that the needle of the assembly is being fixedly secured by a hook mechanism in the housing.

BACKGROUND OF THE INVENTION

Needle protection devices that utilize a housing that pivots relative to the base are exemplified by a number of U.S. patents assigned to the assignee of the instant application. These include U.S. Pat. Nos. 4,982,842, 5,139,489, 5,154,285, 5,232,454, 5,232,455, 5,277,311 and 5,423,765, among others. There are other patents also assigned to the assignee of the instant invention that disclose the anchoring of the housing to the base of a needle. In U.S. patents RE37,110, RE37,252 and U.S. Pat. No. 6,328,713, there is disclosed the mating of an anchor at the base to an opening at the housing. Although feasible, it has been found that such embodiment entails the need for an anchor that has to be of a given length, as well as an opening that has to be well defined. Moreover, the portion of the housing where the opening is to be provided has to be sufficiently thin so as to provide the flexibility that enables the anchor to first pierce through and then be anchored to the opening. Further, with the anchor piercing through the housing, given that contaminated blood may well be splattered to the anchor as the housing closes over the contaminated needle, there may be a chance that contaminated fluid from the needle may be exposed on the backside of the housing where the anchor protrudes. Furthermore, such anchor based needle protection device is difficult to implement with a hook mechanism inside the housing, as the contact between the anchor and the opening at the housing would conflict with the retention of the needle by a hook in the housing, as exemplified by the aforenoted U.S. Pat. No. 4,982,842.

SUMMARY OF THE INVENTION

The present invention safety needle device has a locking mechanism that has one portion extending from the back wall of the housing and another portion extending from the base in such a way that when the housing is pivoted toward the base to cover the needle that extends from the base, the portions of the catch mechanism would couple together to fixedly retain the housing and the base relative to each other. One portion of the catch mechanism is configured to have two fingers closing in on a slot through which the other portion of the catch mechanism, in the form of an elongated anchor or projection, snaps into and be held by the fingers. The two portions of the catch mechanism are designed such that they would matingly couple at substantially the same time as the needle is clasped and be retained by an integral hook in the housing. This configuration ensures that a single pivoting movement of the housing relative to the base would enable the hook in the housing to fixedly retain the needle and at the same time enable the housing and the base be fixedly retained relative to each other. Two flaps each extending from a side wall of the housing prevent further access to the portions of the catch mechanism once those portions are coupled to each other. Each portion in turn may be considered a catch mechanism so that the safety device of the instant invention may be considered to have two coacting catch mechanisms.

The safety needle device of the instant invention is formed from the same mold such that the housing, the base, the portions of the catch mechanism as well as the hook, are integrally formed as a single unitary unit. The needle is fitted to the distal end of the base while the proximal end of the base is configured to be adaptable to a syringe or other medical apparatus for either withdrawing fluid from or ejecting medication to a patient. The needle that is attached to the base of the safety device of the instant invention may be of different gauges. To signify the gauge of the needle, the housing and the base of the safety device are color coded to a given color that has been predetermined to correspond to that given needle gauge.

The instant invention is therefore a needle assembly that has a base having a needle extending therefrom along a longitudinal axis thereof, a housing pivotally connected to the base with two side walls connected by a back wall, one portion of a catch or lock mechanism extends from the back wall so as to couple to another portion of the catch mechanism that extends from the base, so that once the portions of the catch mechanism are coupled to each other, the housing and the base are fixedly retained relative to each other, with the needle being covered by the housing.

The instant invention also relates to a one-piece needle assembly or safety device that is adaptable to be used with a syringe, with the respective portions of the catch mechanism being provided at the base and the housing per discussed above.

The instant invention further relates to a one-piece needle assembly or safety device that has a base having a needle extending therefrom along a longitudinal axis, a housing pivotally connected to the base and having two side walls connected by a back wall, a pair of adjacent first catches that extend from the back wall, a rib extending from the base orthogonal to the longitudinal axis and a pair of second catches that protrude from the rib, so that when the housing is pivoted towards the base to cover the needle, each of the first catches would mate with a corresponding one of the second catches to fixedly retain the housing and the base relative to each other. One pair of the pairs of first and second catches may be loops while the other pair may be bosses or fingers that the loops would snap over when the housing pivots towards and covers the needle.

The instant invention also relates to a method of manufacturing a safety device or a needle assembly that is matable with a syringe, with the safety device having a housing and a base pivotally connected to each other. The housing has a back wall and two sidewalls together that form a slot through which the needle of the needle assembly passes when the housing is pivoted towards the base to cover the needle. The method comprises the steps of extending one catch mechanism from the back wall of the housing and providing another catch mechanism at a location at the base that would ensure that the one and other catch mechanisms are non-removably interlocked to each other when the housing is pivoted to cover the needle. The method of the instant invention also provides for the extending of a rib from the base in a direction facing the housing and the providing of a boss at each side of the rib, and a pair of loops provided as the catch mechanism that extends from the back wall of the housing.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figure 1:
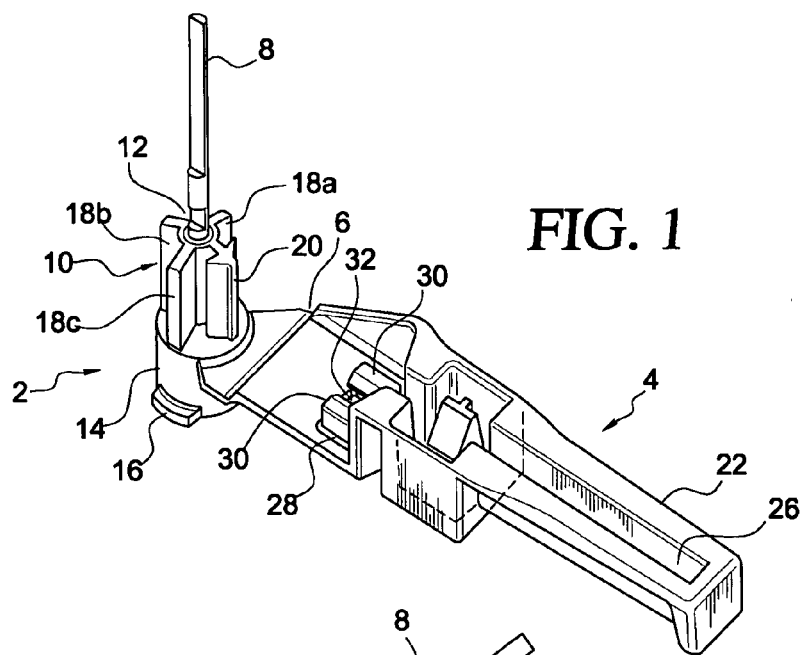
FIG. 1 is a perspective view of the safety device of the instant invention in a free standing position, with the housing being cross-sectioned.

With reference to the figures, the safety device of the instant invention is a needle assembly that has a base 2 and a housing 4 pivotally connected to the base by a living hinge 6. A needle 8 is adaptable to be fitted to the distal portion 10 of base 2. Needle 8 may be molded to the distal end 12 of base 2, or may be fitted thereto after the safety device has been removed from the mold. The proximal portion 14 of base 2 is configured to have a cavity that is adaptable to mate with a syringe, or other fluid storing devices, not shown. A luer connector 16 is provided at base 2.

There are a number of extensions, or ribs, 18a-18c provided at the distal portion 10 of base 2. There is moreover a catch mechanism 20 that extends from distal portion 10 of base 2 at a location facing housing 4. Catch mechanism 20 may be considered as one portion of an overall catch or locking mechanism, as explained below.

Figure 2:
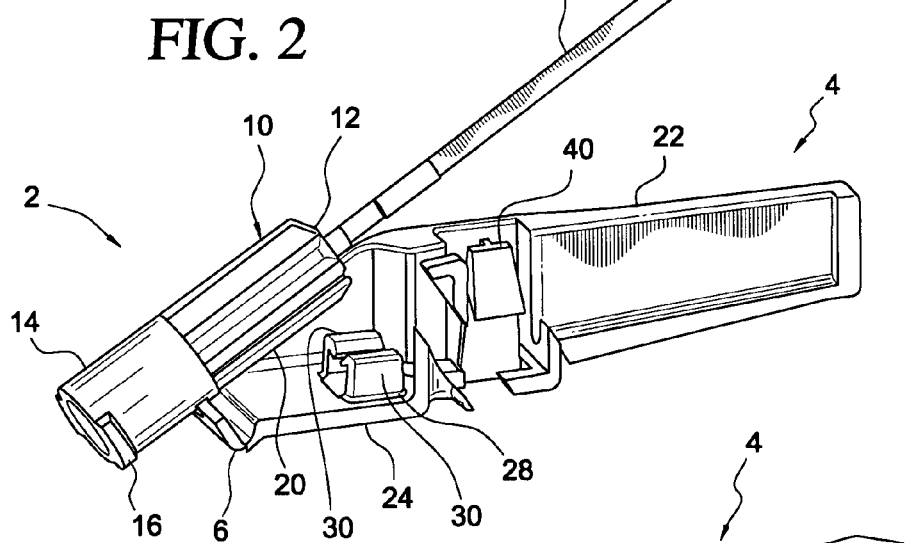
FIG. 2 is a view of the safety device of the instant invention, with the housing being shown in cross-section, as the housing and the base of the device are moved relatively towards each other.

Housing 4 is connected to base 2 via living hinge 6. Housing 4 has two sidewalls 22 connected by a back wall 24. A slot or passage 26 for housing 4 is defined by sidewalls 22. It is through passage 26 that needle 8 passes when housing 4 and base 2 are pivoted relative to each other, as shown in FIG. 2.

Figure 5:
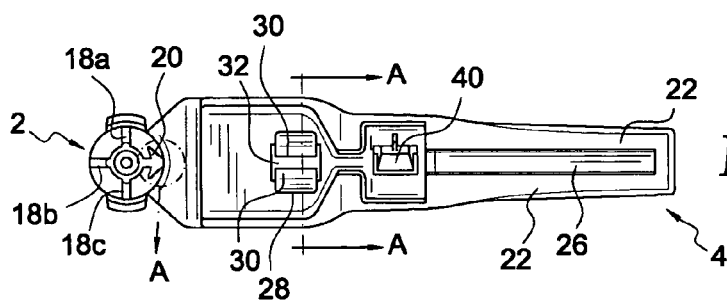
FIG. 5 is a top view of the safety device of FIG. 4.
Figure 6:
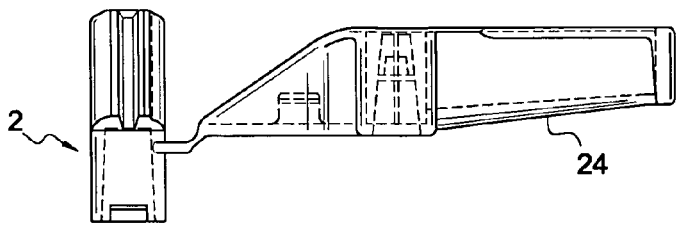
FIG. 6 is a side view of the safety device of FIG. 4.
Figure 7:
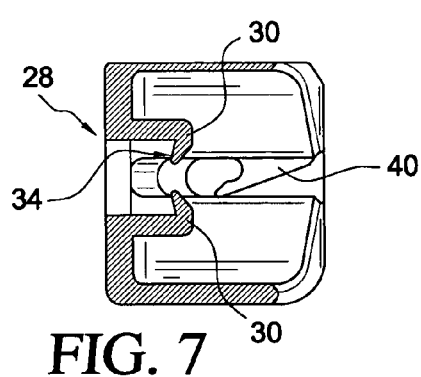
FIG. 7 shows the view at cross-section A-A of FIG. 5.

Extending from back wall 24 is a second catch or locking mechanism 28 that includes two grasping fingers 30. An opening 32 is configured between the grasping fingers 30. As best shown in FIG. 5 and the cross-sectional view in FIG. 7, each of the fingers 30 is configured to fold inward per its fingertip 34. The space defined by the fingers 30 is dimensioned to accommodate catch mechanism 20 at base 2 of the device, as best shown in FIG. 5 and the enlarged view thereof in FIG. 8.

Figure 3:
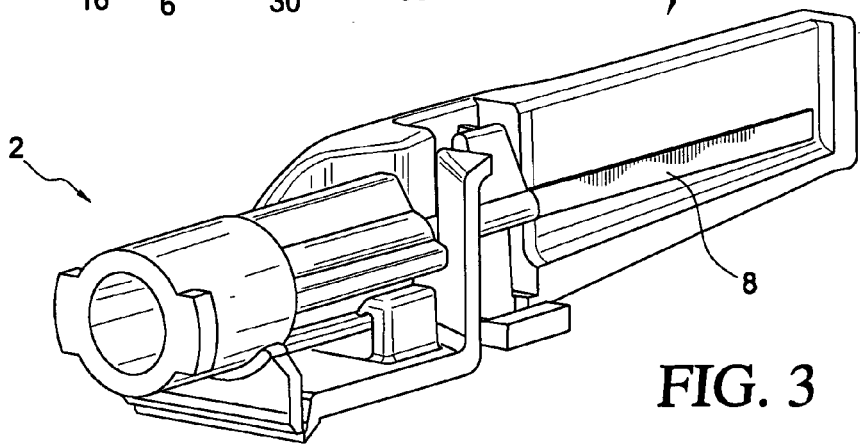
FIG. 3 shows the device in a fully actuated position with the locking snaps of the catch mechanism engaged.
Figure 4:
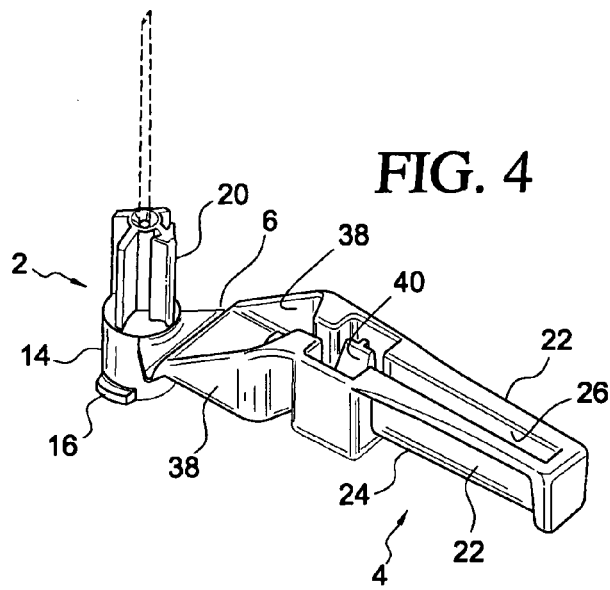
FIG. 4 is another perspective view of the device of the instant invention.
Figure 8:
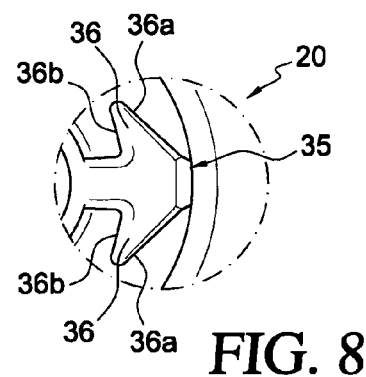
FIG. 8 is an enlarged view of detail A as shown in FIG. 5.

Catch mechanism 20 for the embodiment shown in FIG. 8 is in the form of an anchor or a projection that extends longitudinally along the distal portion 10 of base 2. Anchor 20 has a front surface 35 and two arrow shaped extensions 36. As the front surfaces 36A of the extensions 36 are inclined at an angle, when catch mechanism 20 meets with catch mechanism 28, the anchor extensions 36 would readily coact with the slant inward tips of fingers 30 to thereby readily engage with those fingers. The back surfaces 36b of catch mechanism 20 and the inwards folding finger tips 34 of catch mechanism 30 coact to prevent catch mechanism 20 and catch mechanism 30 from being removed from each other, thereby securely and non-removably coupling housing 4 to base 2. Thus, as best shown in FIGS. 2 and 3, when housing 4 and base 2 are pivoted relative to each other, as catch mechanism 20 at base 2 meets catch mechanism 28 at housing 4, catch mechanism 20 would snap into catch mechanism 30 so that both catch mechanisms interlock with each other, as best shown in FIG. 3. As discussed previously, catch mechanisms 20 and 28 may each be considered a portion of an overall catch or interlocking mechanism of the safety device of the instant invention.

Each of the sidewalls 22 has an extension 38 at its proximal portion. Together the side extensions 38 provide a protective environment for catch mechanism 28 that extends from the back wall 24 of housing 4. When catch mechanism 28 is interlocked with catch mechanism 20 as housing 4 is pivoted toward base 2 and covers needle 8, the side extensions 38 of housing 4 would prevent further access to the interlocked catch mechanisms to thereby impede any attempt to remove housing 4 from base 2.

Also integrated to housing 4 is a hook mechanism 40 that acts to clasp needle 8, when housing 4 is pivoted toward base 4 to cover needle 8. Hook 40 fixedly retains needle 8, once needle 8 snaps past the lip portion of hook 4 and is retained by the backside of the lip of hook 40.

As best shown in FIG. 2, the placement of hook mechanism 40 and catch mechanism 28, as well as the extension of those mechanisms from the back wall 24 of housing 4, are such that when housing 4 and base 2 are relatively pivoted toward each other, both needle 8 and catch mechanism 20 would make contact at substantially the same time with hook mechanism 40 and catch mechanism 28, respectively, so that both needle 8 and base 4 are secured to housing 4 at substantially the same time. By providing a combined interlocking of the needle and the base to the back wall of housing 4, needle 8 is ensured to be securely covered by housing 4 and not be re-exposed to the environment.

By providing catch mechanisms that extend from the back wall of the housing and from the base, and further configuring catch mechanism 20 to extend longitudinally along the distal portion of base 2, the coupling of housing 4 to base 2 is ensured to be more secured, as the coupling of housing 4 and base 2 is effected by the interlocking of the catch mechanisms as well as the clasping of needle 8 by hook 40. Thus, by effecting two catch points from the back wall of the housing, i.e., the interlocking of the catch mechanisms and the clasping of the needle by the hook, the housing is more securely held to the base to thereby ensure that the needle is securely covered. Further, by preventing access to the interlocked catch mechanisms, needle 8 could not be unlatched from hook 40.

Base 2 and housing 4, as well as the catch mechanisms 20 and 28 and hook 40, are formed as an integral unitary unit from the same mold. It may, for example, be injection molded.

Prior to use, needle 8 may be covered by a sheath, not shown, that fits over distal portion 10 of base 2. Further, the safety device of the instant invention may be molded or fitted with a number of different needles each having a different gauge. For the instant invention needle assembly, depending on the gauge of the needle fitted to the base, the safety device may be color coded to a predetermined color so that, without looking at needle 8 which is covered by the sheath, a user can readily ascertain the gauge of the needle. Thus, the molded one-piece unit of the safety device of the instant invention is color coded to have a predetermined color that signifies the gauge of the particular needle that is attached to its base. A more detailed discussion of such color coding of the needle to the body of the device is provided in application Ser. No. 10/751,982 having filing date of Jan. 7, 2004. The disclosure of the '982 application is incorporated by reference herein.

Figure 9:
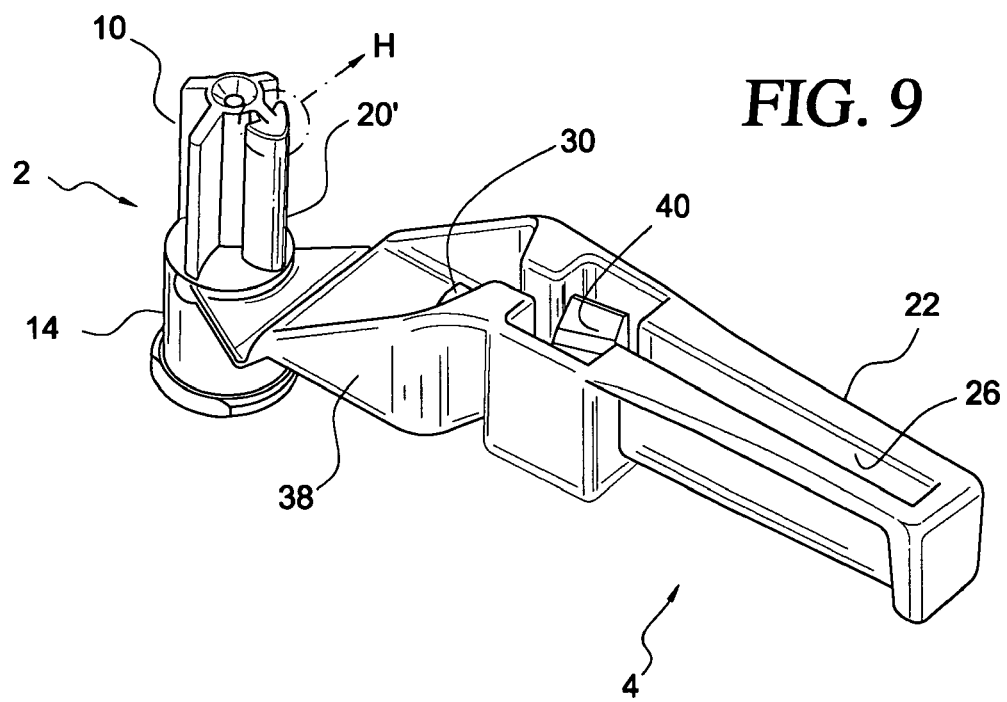
FIG. 9 is a perspective view of the instant invention safety device that has an alternative catch mechanism at the base of the device.
Figure 10:
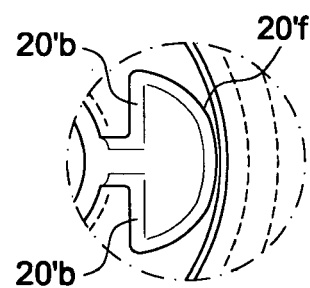
FIG. 10 is an enlarged detail of the alternative catch mechanism.
Figure 11:
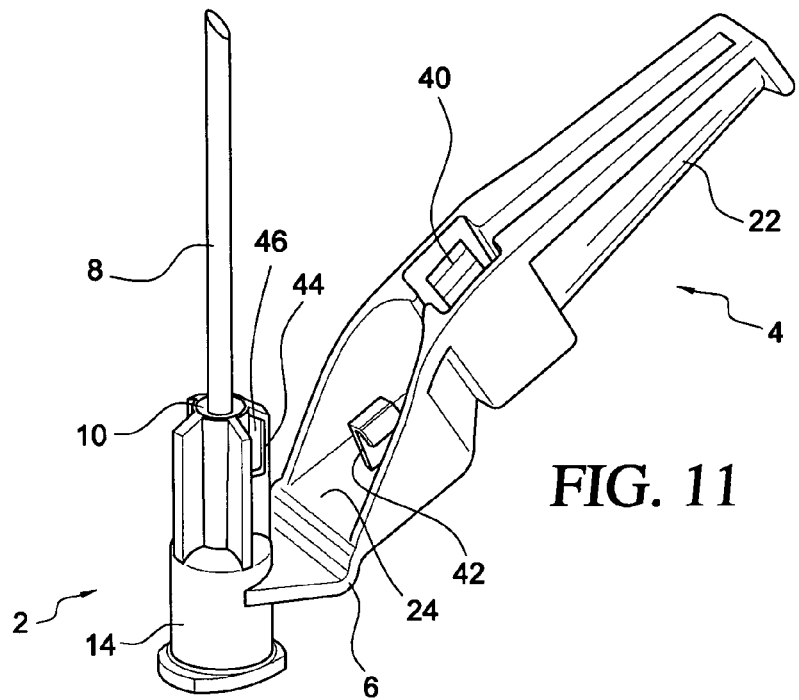
FIG. 11 is another embodiment of the instant invention safety device in which alternative catch mechanisms are provided at the base and the housing of the device.

An alternative embodiment of the catch mechanism at the base of the safety device is shown in FIGS. 9 and 10. The difference between the device shown in FIG. 9 and that shown in FIGS. 1-8 is the configuration of the anchor or projection 20'. As shown in greater detail in FIG. 10, catch mechanism 20' has a front surface 20'f that is curved, in contrast to the inclined side surfaces 36a of catch mechanism 20, as shown in FIG. 8. Furthermore, the back surfaces 20'b of projection 20' are not inwardly angled. The configuration of the tips of the respective fingers 30 could be adjusted to ensure that those fingertips could fixedly grasp onto the respective back surfaces 20'b, once the head of projection 20' is moved between the fingers and passed the fingertips. Like the previous embodiment, catch mechanisms 30 and 20' make contact substantially at the same time as hook 40 makes contact with the needle, not shown, that extends from the distal end 10 of base 2.

Figure 12:
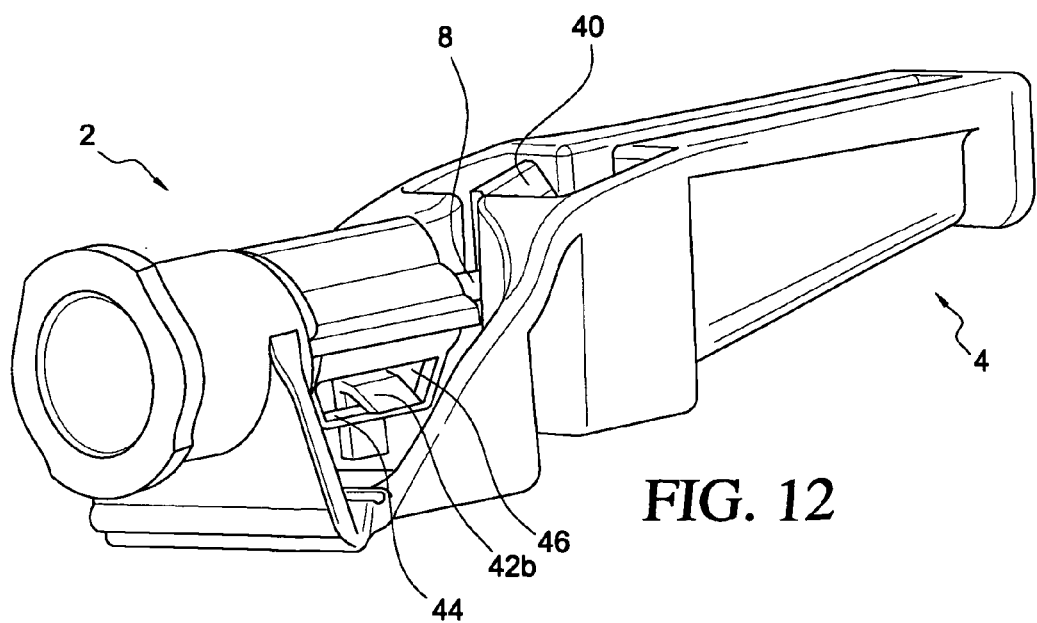
FIG. 12 illustrates the safety device of FIG. 11 in which the housing has been coupled to the base, with the catch mechanisms interlocked.
Figure 13:
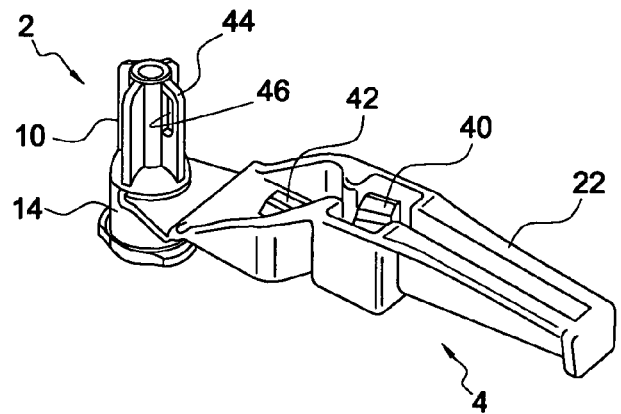
FIG. 13 is a perspective view of the device of FIG. 11.
Figure 17:
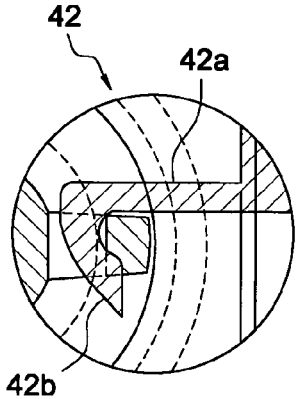
FIG. 17 is an enlarged detail of the other catch mechanism of the safety device of FIG. 13.
Figure 15:
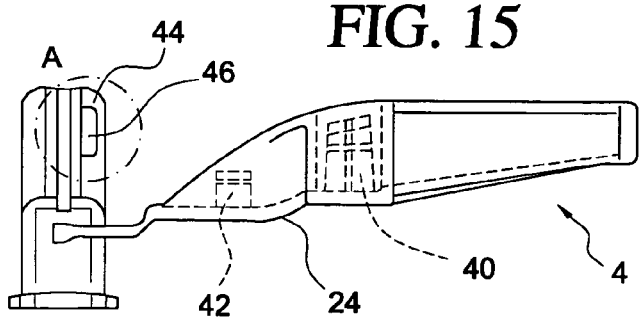
FIG. 15 is a side view of the FIG. 13 safety device.

The catch mechanisms for the safety device shown in FIGS. 11-15 are different from those shown earlier. Specifically, the catch mechanism extending from the back wall 24 of housing 4 is configured in the form of a hook 42, as best shown by the enlarged detail illustration of FIG. 17. There it can be seen that hook 42 has an extension 42a and a tip 42b. Coacting with hook 42, at the distal portion 10 of base 2 of the safety device, is a latch in the form of a rib 44 that extends substantially longitudinally along the length of the distal portion 10 of base 2. An opening 46 is provided in rib 44. It is through opening 46 that the tip 42b of hook 42 latches onto, when housing 4 and base 2 are moved relatively toward each other. As best shown in the fully actuated position of FIG. 19, when hook 42 is interlocked with rib 44, housing 4 and base 2 of the safety device are fixedly retained relative to each other. FIG. 12 shows the fingertip 42b of hook 42 extending through opening 46 of rib 44, to thereby firmly latch onto rib 44. FIG. 12 also shows needle 8 being grasped by hook 40. Thus, a double hook safety device is effectuated by the embodiment of the safety device shown in FIGS. 11-15.

Figure 16:
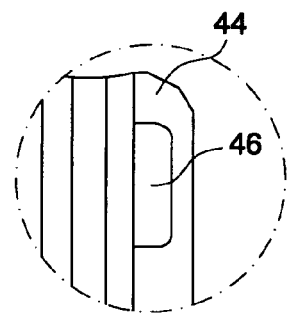
FIG. 16 is an enlarged detail of the catch mechanism at the base of the safety device of FIG. 13.
Figure 14:
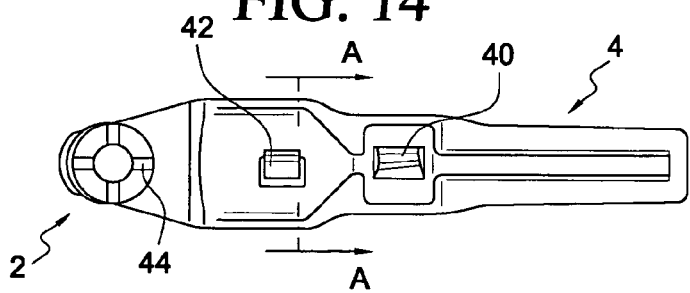
FIG. 14 is a plan view of the FIG. 13 safety device.
Figure 18:
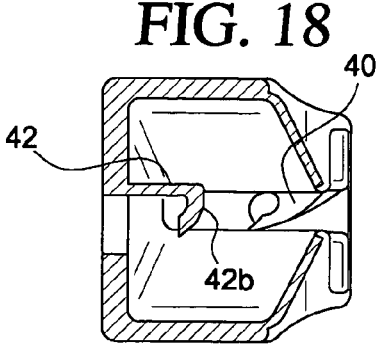
FIG. 18 is a sectional view of the catch mechanism at the housing of the safety device of FIG. 13.
Figure 19:
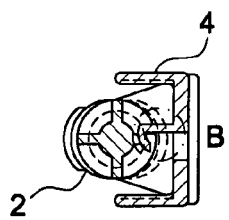
FIG. 19 is a cross-sectional view showing the interlocking of the catch mechanisms of the safety device of FIG. 13.

FIG. 14 is a plan view of housing 4, which is shown to have been pivoted away from base 2. In this view, both hooks 40 and 42 are clearly shown. The same is true with respect to the side view of the safety device shown in FIG. 15, where rib 44, and its opening 46, are clearly shown. The enlarged detail of the latch rib is shown in FIG. 16. The cross-sectional view A-A of the FIG. 13 safety device is shown in FIG. 18. As was noted previously, the fully actuated safety device whereby the catch mechanisms at the housing and base are fully interlocked is shown in FIG. 19.

Figure 20:
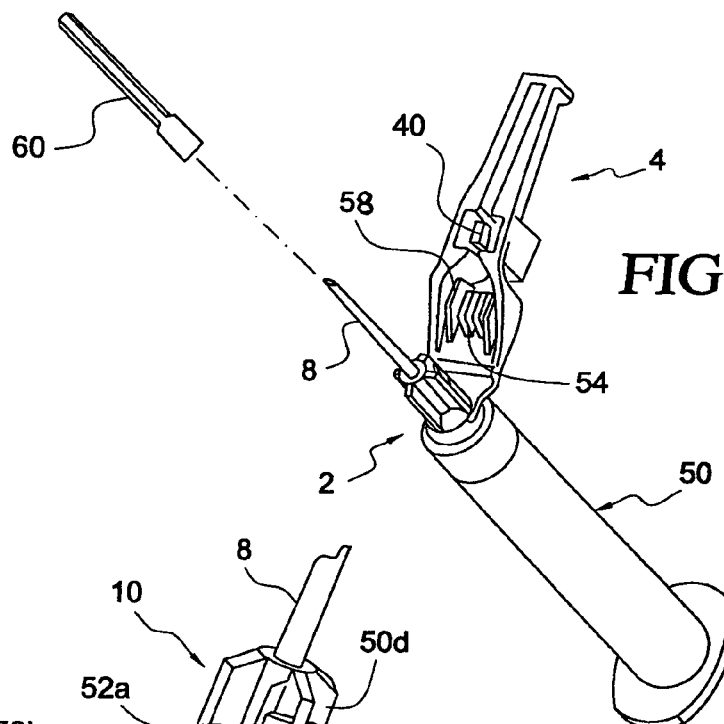
FIG. 20 is a perspective view of a syringe having connected thereto another embodiment of the needle assembly of the instant invention.
Figure 21:
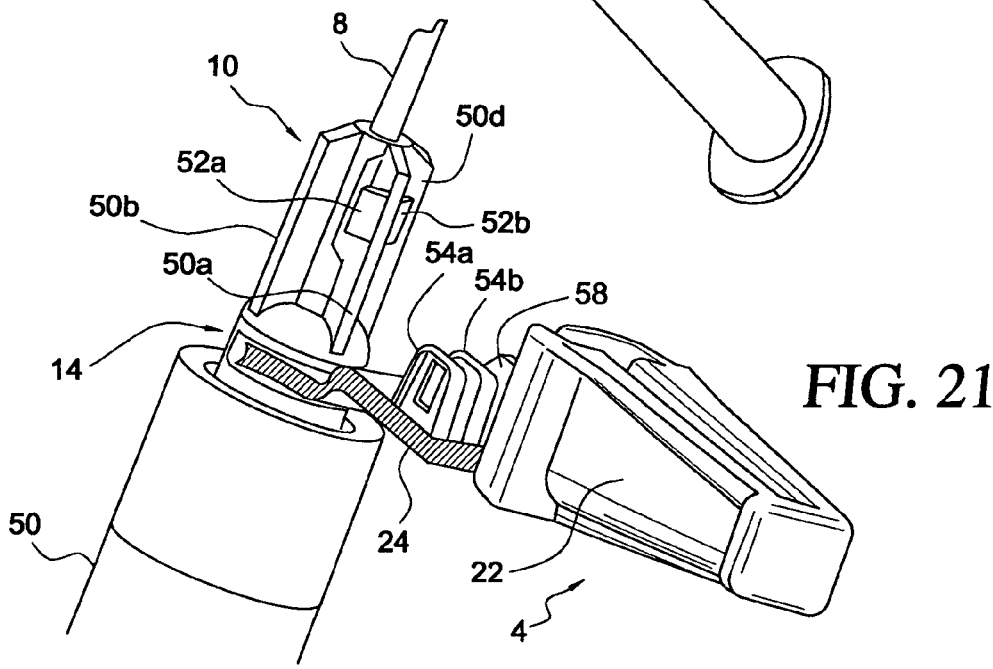
FIG. 21 is a partially cut-away perspective view the embodiment of the needle assembly of FIG. 20.
Figure 22:
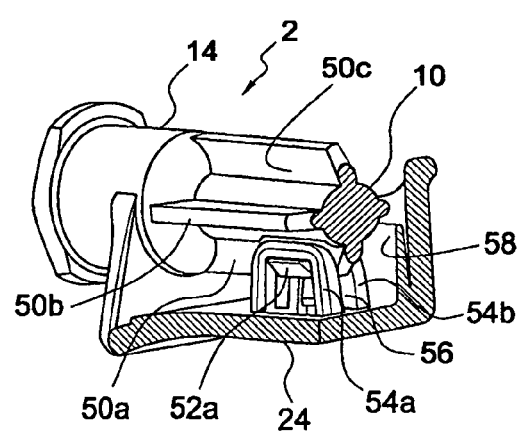
FIG. 22 is a partial sectional view of the needle assembly of FIG. 21 showing a catch mechanism extending from the back wall of the housing mated to a catch mechanism provided at the rib of the base that faces the housing.

Another embodiment of the present invention is shown in FIGS. 20-22. Elements for this embodiment that are same as the earlier embodiments are labeled the same.

In particular, the needle assembly of FIG. 20 is shown to have been matingly connected to a syringe 50. Similar to the earlier embodiments, the safety device or needle assembly of FIG. 20 has a housing 4 hingedly connected to a base 2. As shown in FIGS. 21 and 22, base 2 has a proximal end 14 and a distal end 10. At the distal portion of the needle assembly there are a number of ribs or extensions 50a-50d that extend from base 2. At rib 50a, which extends orthogonally from the longitudinal axis of base 2 (as defined by needle 8) to face housing 4 as housing 4 is pivoted towards base 2, there are provided at the planar sides of rib 50a two fingers or bosses 52a and 52b. As best shown in FIG. 22, bosses 52 each are configured to have a finger portion for grasping and fixedly retaining a corresponding loop or ring 54a and 54b that extend from the back wall 24 of housing 4, when housing 4 is pivoted to cover needle 8. For the embodiment of FIGS. 20-22, the loops 54a and 54b may be considered as one catch mechanism or catches while bosses 52a and 52 may be considered as another catch mechanism or catches. As shown in FIGS. 21 and 22, loops 54a and 54b extend from back wall 24 of housing 4 in an adjacent fashion leaving a space 56 therebetween. Space 56 is configured to be of a given width so that, as loops 54a and 54b coactingly mate with bosses 52a and 52b, respectively, rib 50a is sandwiched by loops 54a and 54b.

In addition to providing rigidity, the multiple ribs 50 are configured to allow the open end of a needle protection sheath 60 that covers needle 8 prior to use to be frictionally fitted thereabout.

Further provided as part of housing 4 in the embodiment of FIGS. 20-22 are a pair of partition walls, or simply partitions 58, that also extend from back wall 24 of housing 4. Each of partitions 58 is interposed between one of the loops 54 and one of the sidewalls 22 of housing 4. As shown in FIG. 22, once the loops 54 snap over and are secured to the respective bosses 52 and needle 8 is covered by housing 4, the front edge of each of the partitions 58 would either come into contact with, or be in very close proximity to, respective ribs 50b and 50d, so that the engaged or interlocked bosses/loops are prevented from being accessed, and possibly tampered with. This is a safety measure that is in addition to the previously discussed segments 38 of the sidewalls of the housing being used to preclude someone from accessing the catch mechanisms, after the catch mechanisms have been mated to securely retain housing 4 and base 2 relative to each other.

As with the other embodiments, a mechanism such as a hook 40 is integrated in housing 4 for grasping needle 8, when housing 4 is pivoted towards base 2 to cover needle 8. Hook 40 and the respective boss and loop catch mechanisms are designed such that hook 40 would come into contact with and grasp needle 8 at substantially the same time that loops 54 snap over and are secured to bosses 52.

As with the other embodiments previously disclosed, the needle assembly of FIGS. 20 to 22 may be made as an integral unit and may be color coded to different predetermined colors for signifying the different gauges of needles that may extend from the needle assembly.

The invention claimed is:

1. A needle assembly, comprising:
   a base having a needle extending therefrom along a longitudinal axis thereof;
   a housing pivotally connected to said base, said housing having two sidewalls connected by a back wall;
   a pair of adjacent first catches that are not part of the sidewalls extending from the back wall between the sidewalls;
   a rib extending from said base orthogonal to the longitudinal axis to face the back wall of said housing; and
   a pair of second catches protruding from said rib;
   wherein each of said first catches mates with a corresponding one of said second catches to fixedly retain said housing and said base relative to each other when said housing is pivoted towards said base to cover the needle.

2. Needle assembly of claim 1, wherein said rib is sandwiched by said first catches when said second catches are respectively mated to said first catches.

3. Needle assembly of claim 1, wherein one pair of said pairs of said first and second catches being loops and the other of said pairs of said first and second catches being bosses, and wherein each of said loops snaps over and secure to a corresponding one of said bosses when said housing pivots toward and covers said needle.

4. Needle assembly of claim 1, further comprising:
   a pair of partitions extending from said back wall of said housing, each partition interposed between one of the sidewalls and a corresponding one of said first catches so that said first catches are sandwiched by said partitions which in turn are sandwiched by said side walls.

5. Needle assembly of claim 1, wherein said base comprises a plurality of ribs together adapted to frictionally accept a proximal portion of a sheath that covers the needle prior to the needle being used.

6. Needle assembly of claim 1, wherein said housing further comprises a hook mechanism for grasping the needle at approximately the same time that said bosses mate respectively with said catches.

7. Needle assembly of claim 1, wherein said base is matable to a syringe.

8. A one piece needle assembly adaptable to be used with a syringe, comprising: a base having pivotally connected thereto a housing, said housing having two side walls connected by a back wall and a pair of adjacent first catch mechanisms that are not part of the side walls extending from the back wall between the side walls that meet with a pair of second catch mechanisms extending from a rib extending from said base to face the back wall of said housing when said housing is pivoted toward said base to cover a needle extending longitudinally from said base, said first and second pairs of catch mechanisms interlocked to each other to prevent said housing and said base from moving away from each other when said needle is covered by said housing.

9. Needle assembly of claim 8, wherein each of said first catch mechanisms comprises a loop that is not part of the side walls and wherein each of said second catch mechanisms comprises a boss provided at a planar side of said rib, said each boss matingly coacting with a corresponding said each loop when said housing is pivoted towards said base.

10. Needle assembly of claim 8, wherein said rib is sandwiched by said pair of first catch mechanisms and said first and second pairs of catch mechanisms are sandwiched by the side walls of said housing when said first catch mechanisms are interlocked with said second pair of catch mechanisms.

11. Needle assembly of claim 8, further comprising:
   a pair of partitions that are not part of the side walls extending from said back wall of said housing, each partition interposed between one of the sidewalls and a corresponding one of said first catch mechanisms so that said pair of first catch mechanisms are sandwiched by said pair of partitions and the side walls.

12. Needle assembly of claim 11, wherein the front edge of each of said partitions either comes into contact with or be in close proximity to a corresponding another rib extending from said base substantially orthogonal from said rib wherefrom said second catch mechanisms extend.

13. Needle assembly of claim 8, further comprising a hook extending from said back wall for clasping said needle when said housing is moved to cover said needle, said hook clasping said needle at substantially the same time that said first pair of catch mechanisms interlock with said second pair of catch mechanisms.

14. Needle assembly of claim 8, wherein said housing and said base are molded as a single unit, said housing and said base being color coded a predetermined color that signifies to the gauge of the needle.

15. Needle assembly of claim 8, wherein each of the side walls has an extension at its proximal portion, the extensions of the sidewalls together preventing access to said first and second catch mechanisms when said catch mechanisms are interlocked to each other.

16. A needle assembly, comprising:
   a base having a housing pivotally connected to said base, said housing having two sidewalls connected by said back wall;
   a pair of first catch mechanisms that are not part of the sidewalls extending from said back wall, said pair of first catch mechanisms interposed between said side walls;
   multiple ribs extending orthogonally from said base; at least one of said ribs extending from said base to face the back wall of said housing and having a pair of second catch mechanisms;
   wherein said first catch mechanisms snappingly mate with said second catch mechanisms to fixedly retain said housing and said base relative to each other when said housing is pivoted towards said base, so that said housing is no longer movable away from said base.

17. Needle assembly of claim 16, wherein said pair of first catch mechanisms comprises one pair of loops and said pair of second catch mechanisms comprises bosses on said one rib, wherein each of said loops snaps over and secures to a corresponding one of said bosses when said housing pivots toward said base.

18. Needle assembly of claim 16, further comprising:
   a pair of partitions extending from said back wall of said housing, each partition interposed between said first catch mechanism and a corresponding one of the sidewalls.

19. Needle assembly of claim 16, wherein said housing further comprises a hook for grasping a needle extending from said base at approximately the same time that said first catch mechanism mates with said catch mechanism.

* * * * *